United States Patent [19]

Fellmann et al.

[11] Patent Number: 5,026,940

[45] Date of Patent: Jun. 25, 1991

[54] MANUFACTURE OF 4'4-DIISOPROPYLBIPHENYL

[75] Inventors: Jere Fellmann, Livermore; Paul Wentrcek, Redwood City; Phat T. Lu, San Jose, all of Calif.

[73] Assignee: Catalytica, Inc., Mountain View, Calif.

[21] Appl. No.: 404,665

[22] Filed: Sep. 8, 1989

[51] Int. Cl.$^5$ .................................................. C07C 2/68
[52] U.S. Cl. ................................... 585/467; 585/466
[58] Field of Search .................................. 585/466, 467

[56] References Cited

U.S. PATENT DOCUMENTS

| | | | |
|---|---|---|---|
| 3,251,897 | 5/1966 | Wise | 585/455 |
| 4,026,959 | 5/1977 | Kemme et al. | 585/320 |
| 4,064,068 | 12/1977 | Haseltime, Jr. | 252/364 |
| 4,179,472 | 12/1979 | Cobb | 585/411 |
| 4,415,544 | 11/1983 | Kokotailo et al. | 423/328 |
| 4,469,908 | 9/1984 | Burress | 585/467 |
| 4,480,142 | 10/1984 | Cobb | 585/466 |
| 4,567,029 | 1/1986 | Wilson et al. | 502/208 |
| 4,795,847 | 1/1989 | Weitkamp et al. | 585/467 |

FOREIGN PATENT DOCUMENTS

| | | |
|---|---|---|
| 0294759 | 12/1965 | Australia . |
| 0654720 | 12/1962 | Canada . |
| 0012514 | 6/1980 | European Pat. Off. . |
| 0202752 | 11/1986 | European Pat. Off. . |
| 285280 | 10/1988 | European Pat. Off. . |
| 288582 | 11/1988 | European Pat. Off. . |
| 0317907 | 5/1989 | European Pat. Off. . |
| 75010586B | 4/1975 | Japan . |
| 75011379B | 4/1975 | Japan . |
| 62226931 | 10/1987 | Japan . |
| 6314738 | 1/1988 | Japan . |
| 63122635 | 5/1988 | Japan . |
| 2199590A | 7/1988 | United Kingdom . |

OTHER PUBLICATIONS

D. B. Priddy, "Alkylation of Biphenyl Under Mild Friedel Crafts Conditions", *I & EC Product Research and Development*, vol. 8, No. 3, Sep. 1969.

K. Hyska, Chem. Prun., 1971.

E. G. Derouane, "Diffusion and Shape-Selective Catalysts in Zeolites", *Intercalation Chemistry*, E.d. by M. Stanley Whittingham (Academic Press, 1982).

J. M. Bennett et al., Zeolites 7, (1987) and P. A. Jacobs, et al., "Synthesis of High Silica Alumino-Silicate Zeolites", Studies in Surface Science and Catalysis, No. 33, Elsevier, 1987.

Meier, W. M. and Olson, D. H., "Atlas of Zeolite Structure Types", 2nd Ed., *Structure Commission of the International Zeolite Association*, Butterworhts, 1987.

Lee, et al., Catalyst Letters 2, (1989).

*Primary Examiner*—Patrick P. Garvin
*Assistant Examiner*—E. D. Irzinski
*Attorney, Agent, or Firm*—E. Thomas Wheelock

[57] ABSTRACT

The selective isopropylation of biphenyl or 4-isopropylbiphenyl to diisopropylbiphenyl while maximizing the yield of the 4,4'-diisopropoylbiphenyl isomer is achieved by carrying out the reaction in the presence of an acidic crystalline molecular sieve with pore aperture 5.7-6.1 Å, preferably SAPO-11 or ZSM-12.

10 Claims, No Drawings

MANUFACTURE OF 4'4-DIISOPROPYLBIPHENYL

TECHNICAL FIELD OF INVENTION

This invention relates to the production of 4,4'-diisopropylbiphenyl through the alkylation of biphenyl compounds. Various shape selective catalysts such as ZSM-12 have been found to maximize the yield of this isomer which is useful as a monomer precursor for liquid crystal polymers.

BACKGROUND OF THE INVENTION

The compounds 4,4'-dihydroxybiphenyl and 4,4'-dicarboxybiphenyl are taught to be key monomers used as precursors for liquid crystal polymers and polyester film. 4,4'-dihydroxybiphenyl is currently prepared by a multi-step route and is not readily available for general use. 4,4'-diisopropylbiphenyl can be readily converted to either monomer by oxidation under the appropriate conditions. Accordingly, these monomers are prepared following equations 1 and 2.

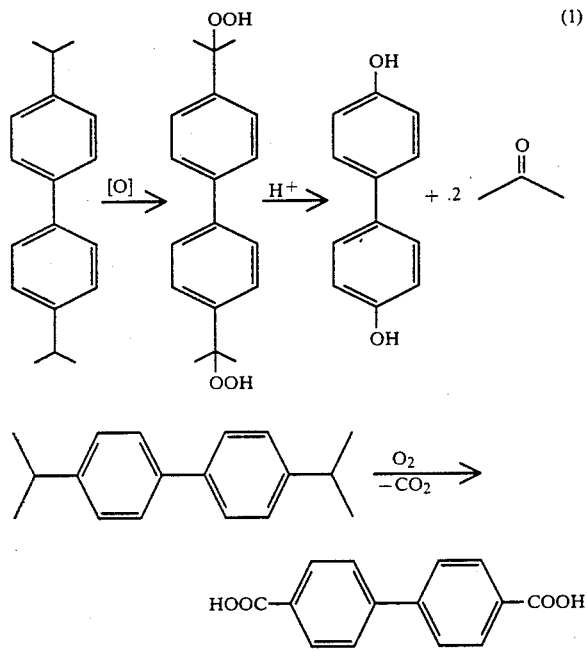

It is generally accepted procedure to provide a numbering scheme for identifying the various isomers of biphenyl as follows:

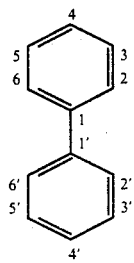

Obviously, the isomers derived from substitution in the 2, 3 and 4 positions are denoted as ortho, meta and para isomers, respectively.

The various combination of isomers of isopropyl alkylates of biphenyl are shown in Table I.

| Isomers of Isopropyl Alkylates of Biphenyl | | |
|---|---|---|
| Alkylate | Total Number | Isomer |
| Mono-IPBP | 3 | o, m, p |
| Di-DIPBP | 10 | 2,6; 2,4; 2,5; 3,5; 2,2'; 2,3'; 2,4'; 3,3'; 3,4'; 4,4' |

As noted from the above table, the mono-alkylate of biphenyl has three possible isomers. These are derived from substitution of, in this case, propylene in the 2, 3 and 4 positions.

Dialkylation of biphenyl can occur in two ways, same ring and adjacent ring disubstitution. For same ring alkylation, it is likely that no ortho disubstitution can take place due to the stearic bulk of the isopropyl group. For same ring alkylation, the isomers expected are the 2,6; 2,4; 2,5; and 3,5. A greater number of isomers are possible for adjacent ring disubstitution, namely, 2,2'; 2,3'; 2,4'; 3,3'; 3,4;' and 4,4'. For the trialkylate, there are many more possible isomers making the total number of products possible in a typical alkylation of biphenyl with a non-shape selective catalyst quite large. If high conversion to diisopropylbiphenyl is sought, it is possible to create tetraalkylates complicating the mixture of products even further. As such, it is imperative for the practicality of any process for the production of 4,4'-diisopropylbiphenyl that the number of isomers be reduced so that the recycle and re-equilibration of by-products be minimized.

The alkylation of biphenyl with olefins is a well known reaction. For example, K. Hyska teaches in Chem. Prun. 1971, 21, pp.264–70, that $AlCl_3$ can be used as a catalyst for the propylation of biphenyl. However, the 3- and 4- isomers predominate for the case of the monoalkylate and complex mixtures of the dialkylate are present as reaction products. In addition, U.S. Pat. No. 4,480,142 discloses the use of NAFLON as a catalyst which gives an enhancement to the 2-alkyl products. This is probably due to the low reaction temperature of approximately 200° C. taught by the referenced patent, as a result, the 2-isomer becomes the preferred product. As a result, the total amount of the 3,3', 3,4' and 4,4' isomers is low since the concentration of 3- and 4- isopropylbiphenyl is also low.

Notably, the selective preparation of 4,4'-diisopropylbiphenyl is taught in Japanese Kokai 63-122635. The Japanese reference teaches that the 4,4'-isomer can be made in relatively high selectivity using a mordenite zeolite catalyst while combining biphenyl with propylene at elevated pressures. The use of mordenite as the preferred catalyst was further substantiated by a recent report by Lee et al. (Catalysis Letters 2 (1989) 243–248). In this reference the author teaches the preference of a specific zeolite source and treatment by a dealumination procedure to obtain a suitable catalyst.

It was the object of the present invention to improve upon the selectivity which is taught in these references while avoiding the necessity for operating at either elevated pressures or treating the mordenite catalysts by costly and cumbersome dealumination procedures. It is particularly important to minimize the amount of propylene in contact with the catalyst at any given time. This is necessary in order to maximize the catalyst life since it is well known in the art that olefins can lead to the generation of carbonaceous residues on the surface of the zeolite catalyst thereby causing the catalyst to deactivate. As a result, the effective shape selective catalyst of this invention must be operated in such a manner as to minimize the propylene contact with the shape selective catalyst. This can be accomplished most effectively by operating at low propylene pressures. It is a further object of this invention to provide shape selective catalysts whose pore size and configuration are such that they maximize the yield of the desired 4,4'-diisopropylbiphenyl isomer relative to the sum of the other dialkylate species while minimizing the formation of higher substituted species. It has thus been determined that when the mordenite zeolite catalyst of these references is replaced by SAPO-11 or preferably ZSM-12 as the acidic crystalline molecular sieve of choice, the selectivity of 4,4'-diisopropylbiphenyl is enhanced while obviating the need for dealumination of the mordenite catalyst and operating the reaction at high propylene pressures.

It is sometimes found that beneficial performance, for example longer catalyst life and/or higher catalyst activity, ensues when hydrogen alone or in combination with hydrogen sulfide are added at moderate pressures to the reactants. The advantageous use of hydrogen in this way is often enhanced if a hydrogenating metal, for example nickel or palladium, is incorporated into the zeolite. Hydrogen sulfide is often used to partially deactivate the hydrogenating metal in such a manner as to only hydrogenate diene species present and not olefins or aromatics. A flow system can be used to operate the process of the invention, the unused hydrogen and/or hydrogen sulfide may be removed from the products and recycled.

The zeolite catalyst may be used in the form of suitable aggregates which are prepared by well known techniques, for example with or without a binder such as alumina, or by inclusion into a matrix such as silica-alumina, in a manner analogous to that often used in the manufacture of fluid catalytic cracking catalysts.

If desired, the external surface of the zeolite may be poisoned so as to reduce or remove catalytic activity thereon, especially the catalysis of unwanted reactions, for example the isomerization of the selectively alkylated biphenyl compounds of this invention. In some cases, zeolites treated with magnesium, phosphorous or silicon compounds have beneficial properties in the process of this invention.

SUMMARY OF THE INVENTION

This invention deals with a process which comprises reacting biphenyl or 4-isopropylbiphenyl with propylene in the presence of an acidic molecular sieve catalyst with effective pore aperture 5.5–6.8 Å, preferably SAPO-11 or most preferably ZSM-12, under conditions sufficient to convert biphenyl or 4-isopropyl biphenyl and propylene to 4,4,'-diisopropylbiphenyl. The effective pore aperture dimensions can be more accurately defined by calculating the relative pore diameter described in a recent reference, namely, Derouane et al., *Applied Catalysis.* 40 (1988) L1–L10. Accordingly, the relative pore diameter most preferred by the present invention is between 5.7 and 6.1 angstroms. The relative pore diameters for ZSM-12 and SAPO-11 are 5.72 and 6.06+/−0.05 angstroms, respectively.

DETAILED DESCRIPTION OF THE INVENTION

In order to demonstrate the shape selective effect for the diisopropylation of biphenyl, intrinsic to a particular catalyst it is necessary to establish a base line for a given catalyst. Initial experiments were designed and conducted to achieve an assessment of the equilibrium concentration of mono and dialkylates. In this way, only the zeolite catalysts which show a high selectivity to 4,4'-diisopropylbiphenyl under these reaction conditions are the proper examples of shape selective catalysts. In each case, propylene was fed at a low rate over an $SiO_2/Al_2O_3$ catalyst with a low biphenyl/catalyst ratio, e.g., 9:1. The results which were achieved confirmed that equilibrium was reached since the ratios of the products did not change as the conversion increased. For biphenyl, the dominate monoalkylate was the 3-isomer comprising ca. 63% with 35% being the 4-isomer. The remaining 2% of the product mixture was the 2-isomer. For the dialkylate, the 3,4'-isomer was the predominate product while for known dialkylates, at equilibrium, the ratio of the 3,3'-isomer, 3,4'-isomer and 4,4'-isomer was 2.1:2.8:1. A percent selectivity of 4,4'-diisopropylbiphenyl/total dialkylates higher than 20% and a 4,4'/3,4' ratio greater than 0.36, obtained under these conditions, is evidence for a shape selective effect.

When carried to equilibrium, the 3,4'-isomer was the predominate product. It became apparent that the only way to achieve high selectivity to the 4,4'-isomer was by the use of a shape selective catalyst. It was surprisingly found that the catalysts of choice were SAPO-11 or ZSM-12 which are acidic, crystalline molecular sieves, ZSM-12 being the preferred catalyst.

Crystalline sieve structures are often defined in terms of the number of the tetrahedral units (T. atoms). For example, in sodalite, the silica and alumina tetrahedra are linked together to form a cubooctahedron, an octahedron truncated perpendicularly to all $C_4$-axes. The sodalite unit is built from 4 and 6 member oxygen rings. A more complete characterization of zeolites can be found in E. G. Derouane, "Diffusion and Shape-Selective Catalysis in Zeolites", *Intercalation Chemistry.* Ed. by M. Stanley Whittingham (Academic Press 1982).

SAPO-11 belongs to the family of silicoaluminophosphate molecular sieves, first reported in 1984 in U.S. Pat. No. 4,440,871. The pore structure of SAPO-11 consists of linear, non-interconnected channels which are limited by 10 membered rings and possess pore aperture dimensions of 3.9 Å and 6.3 Å. See Bennett, J. M., et al., Zeolites, 7 (1987) 160. See also Meyer, W. M., and Olson, D. H., "Atlas of Zeolite Structure Types", 2nd Ed., *Structure Commission of the International Zeolite Association,* Butterworths, 1987.

The pore structure of ZSM-12 consists of linear, non-interpenetrating channels which are formed by 12-member rings and possess pore aperture dimensions of 5.5 Å, 5.77 Å and 6.2 Å. See Jacobs, P. A. et al., "Synthesis of High Silica Aluminosilicate Zeolites", Studies in Surface Science and Catalysis, No. 33, Elsevier, 1987, p. 301. See also Meyer, W. M., "Atlas of Zeolite Structure Types", 2nd Ed., *Structure Commission of the International Zeolite Association,* 1987.

Pore structure (dimensions and network) varies greatly among zeolites. Without modifications of the zeolite structure, the smallest pore aperture dimension is about 2.6 Å and the biggest 7.4 Å. Pores may lead to linear, parallel, or interconnected channels or may give access to larger intracrystalline cavities, sometimes referred to as cages. For all zeolites, the pore opening is determined by the free aperture of the oxygen ring that limits the pore aperture.

The free diameter values given in the channel description and on the ring drawings (not shown here) are based upon the atomic coordinates of the type species in the hydrated state and an oxygen radius of 1.35 Å, as determined from x-ray crystallographic data. Both minimum and maximum values are given for non-circular apertures. In some instances, the corresponding interatomic distance vectors are only approximately coplanar; in other cases the plane of the ring is not normal to the direction of the channel. Close inspection of the framework and ring drawings should provide qualitative evidence of these factors. Some ring openings are defined by a very complex arrangement of oxygen atoms. It should be noted that crystallographic free diameters may depend upon the hydration state of the zeolite particularly for the more flexible frameworks. It should also be borne in mind that effective free diameters can be temperature dependent. Maximum values for the four-, six-, eight-, ten-, and twelve-membered oxygen rings have been calculated to be 2.6 Å, 3.6 Å, 4.2 Å, 6.3 Å and 7.4 Å, respectively.

As used throughout the instant specification, the term "pore aperture" is intended to refer to both the pore mouth at the external surface of the crystalline structure, and to the intracrystalline channel, exclusive of cages. When a crystalline molecular sieve is hereinafter characterized by a "pore aperture dimension", this term is intended to adopt the geometric dimensional analysis defined as "crystallographic free diameter of channels" in Meier, W. M., Olson, D. H., *Atlas of Zeolite Structure Types.* (Butterworth's, 1987, 2nd Rev. Ed.). The term "dimension" is preferred over "diameter" because the latter term implies a circular opening, which is not always accurate in crystalline molecular sieves. When citing an "effective pore aperture dimension or width" what is meant is that the non-circular opening of the zeolite is characterized by its longest dimension. For example, ZSM-12 is an irregularly shaped zeolite with pore aperture dimensions of 5.5 Å × 5.7 Å × 6.2 Å. Likewise, SAPO-11 has an effective pore aperture dimension of 3.9 × 6.3 angstroms. A more appropriate description of the pore aperture dimension for non-circular zeolites has been recently described by Derouane et al. Using the calculated relative pore diameter from the said reference yields values of 5.72 and 6.06 angstroms for ZSM-12 and SAPO-11, respectively.

Shape selective reactions occur when the zeolite framework and its pore structure allow substrate molecules of a given size and shape to reach active sites located in the intracrystalline free space, and allow product molecules of a given size and shape to diffuse out of the intracrystalline free space. It is, therefore, important to characterize accurately the pore structure that is encountered in the various crystalline molecular sieve frameworks.

According to the present invention, biphenyl or 4-isopropylbiphenyl is fed to an alkylation reactor together with propylene in the presence a shape selective catalyst such as ZSM-12 which is an acidic, crystalline molecular sieve under conditions sufficient to convert the biphenyl compound and propylene to diisopropylbiphenyl. The reactor can be a fixed bed or trickle bed type of reactor. A batch type such as a stirred tank reactor is suitable as well. The optimum reaction conditions are at low propylene flow rates and low partial pressures of propylene. In addition the contact time must be sufficient to obtain equilibrium distribution of products in the absence of a truly shape selective catalyst. In order to confirm the enhancement of 4,4'-isomer production using the catalysts of the present invention, various other catalysts were employed in the alkylation reactor as well.

The present invention involves the use of a particular zeolite ZSM-12 in its acidic or hydrogen form. It was surprisingly found that ZSM-12 would form 4,4'-diisopropylbiphenyl in high yield by the combination of propylene with biphenyl or 4-isopropylbiphenyl under conditions where equilibrium can be achieved.

The synthesis procedure for ZSM-12 has been described in a previous reference. See Jacobs, et al. "Synthesis of high-Silica Aluminosilicate Zeolites", *Elsevier*, (Amsterdam, 1987, page 303.). Typically, the Si/Al ratio is limited to the lower end of the range of 10 to pure $SiO_2$. The preferable range for this invention is from 10 to 100, most preferably from 15 to 45.

Experimental Conditions

A stirred autoclave reactor was chosen for this work. It is conveniently operated and was suitable for the purposes of screening for selectivity improvements. The experiment is not limited to this type of reactor. A fixed bed or trickle bed reactor would work as well. For convenience, an autoclave was used.

The reactor utilized gaseous propylene. However, the propylene feed rate was regulated via a mass flow controller. By regulating the propylene feed rate, the system could be operated under propylene-limited conditions. These conditions simulate an equilibrium limited reaction.

The analytical results were obtained by gas chromatography. The catalysts were tested in a 300 cc Autoclave Engineers autoclave.

In testing a catalyst, 90 g biphenyl and 2 g of catalyst were charged and gaseous propylene was fed at a constant flow from a mass flow controller. In all cases unless noted, periodic samples were withdrawn and analyzed by GLC. The reaction temperature was 275° C. although the reaction temperature can be varied from 200° to 350° C. The propylene pressure can be from 1 atmosphere to 50 atmospheres, preferably less than 10 atmospheres. All data expressed in the tables are as mole percent selectivity. The methods used in this study to calculate these parameters used for comparing catalyst performance are as follows:

$$\text{Moles "X"} = \frac{\text{Peak Area of "X"}}{\text{Number of Carbons in "X"}}$$

$$\text{Mole Percent "X"} = \frac{\text{Moles "X"}}{\text{Sum of Moles of all Species in Sample}} \times 100$$

$$\text{Mole Percent Selectivity} = \frac{\text{Moles "X"}}{\text{Sum of Moles of All Alkylated Species in Sample}} \times 100$$

$$\% \text{ Conversion} = 100 - \text{Mole Percent Substrate in Sample}$$

$$\% \text{ 4,4-Dialkylate} = \frac{\text{Moles 4,4'}}{\text{Sum of Moles of Dialkylates in Sample}} \times 100$$

$$4,4'/3,4' = \frac{\text{Moles 4,4'}}{\text{Moles 3,4'}}$$

It is recognized that for comparative purposes on issues dealing solely with selectivity that a more useful measure of performance other than selectivity to the 4,4' isomer was needed. Instead, a more convenient measure of relative performance was devised, that is, the 4,4'/3,4' ratio gave an assessment of the primary objective, which was to produce more 4,4' than 3,4'. The % 4,4'/dialkylates gave a measure of the amount of desired isomer produced among all dialkylates.

A series of comparative examples were conducted under equilibrium limiting conditions. In this series, the uniqueness of ZSM-12 over mordenite or any other catalyst is clearly evident (See Table II).

In the third example, the importance of the Si/Al ratio of ZSM-12 is shown. At high ratios the catalyst rapidly deactivates whereas at the lower ratio, the catalyst does not show rapid deactivation. (See Table III).

EXAMPLE 1

In the typical experiment 90 g of biphenyl and 2.0 g of a silica-alumina (SA) catalyst were charged to an autoclave reactor (300 cc) and gaseous propylene was fed at a constant flow from a mass flow controller. THe flow rate was 100 cc/min and the reaction temperature was 275° C. In this way the amount of propylene was at a minimum and the distribution of products were at equilibrium. This was shown by following the 4,4'/3,4' and the % 4,4'/total DIPBP ratios for silica-alumina as a function of conversion. At equilibrium these values are nearly constant (Table I).

TABLE I

| Catalyst | % conv | % IPBP | % DIPBP | % TIPBP | % 4,4'Di | 4,4'/3,4' |
|---|---|---|---|---|---|---|
| SA | 34 | 86 | 13 | 0.4 | 20 | 0.6 |
|  | 61 | 69 | 28 | 2.4 | 19 | 0.6 |
|  | 89 | 40 | 49 | 11 | 17 | 0.5 |

EXAMPLE 2

Following the procedure in Example 1, zeolite catalysts were tested under conditions where an equilibrium distribution of products were obtained with a non-shape selective catalyst. These data show the uniqueness of ZSM-12 and SAPO-11 over mordenite and silica-alumina (SA) as a shape selective catalyst under equilibrium conditions.

TABLE II

| Catalyst | % conv | % IPBP | % DIPBP | % TIPBP | % 4,4'Di | 4,4'/3,4' |
|---|---|---|---|---|---|---|
| SA | 89 | 40 | 49 | 11 | 17 | 0.5 |
| Mordenite | 96 | 37 | 61 | 2 | 19 | 0.4 |
| SAPO-11 | 86 | 41 | 55 | 4 | 18 | 1.4 |
| ZSM-12 | 78 | 69 | 28 | 3 | 65 | 3.4 |

EXAMPLE 3

In order to demonstrate the preferred Si/Al ratio, the following ZSM-12 catalysts were tested according to Example 2. As can be seen, the most preferred catalyst (Si/Al=18) shows a higher rate of alkylation and a longer catalyst lifetime than the less preferred ratio (Si/Al=47). The less preferred catalyst was essentially inactive after 7 hours.

TABLE III

| Si/Al | Time | % conv | % IPBP | % DIPBP | % TIPBP | % 4,4'Di |
|---|---|---|---|---|---|---|
| 18 | 5.8 hr. | 67 | 77 | 21 | 1 | 64 |
| 47 | 7.0 hr. | 46 | 83 | 15 | 1 | 63 |

We claim:

1. A process for producing a diisopropylbiphenyl stream containing more than an equilibrium amount of 4,4'-diisopropylbiphenyl, which process comprises the steps of:
   (a) providing biphenyl or 4-isopropylbiphenyl and propylene to a catalyst characterized as having relative pore diameters between approximately 5.7 and 6.1 Å; and
   (b) reacting said biphenyl or 4-isopropylbiphenyl with propylene in the presence of said catalyst under conditions sufficient to convert said biphenyl or 4-isopropylbiphenyl to 4,4'-diisopropylbiphenyl and thereby produce the diisopropylbiphenyl stream containing 4,4'-diisopropylbiphenyl.

2. The process of claim 1 wherein the diisopropylbiphenyl stream contains both 3,4'-diisopropylbiphenyl and 4,4'-diisopropylbiphenyl and wherein the 4,4'-diisopropylbiphenyl/3,4'-diisopropylbiphenyl ratio is equal to or greater than 0.36 at a temperature higher than 200° C.

3. The process of claim 1 wherein the diisopropylbiphenyl stream additionally comprises dialkylate isomers and the percentage of 4,4'-diisopropylbiphenyl in dialkylate isomers is equal to or greater than 20%.

4. The process of claim 1 wherein said catalyst is a member selected from the group consisting of SAPO-11 and ZMS-12.

5. The process of claim 1 wherein said catalyst is ZSM-12.

6. The process of claim 1 wherein said reaction is not carried at equilibrium.

7. The process of claim 1 wherein said catalyst is characterized as possessing a Si:Al ratio of between approximately 10 to 100.

8. The process of claim 7 wherein said Si:Al ratio is between approximately 15 to 45.

9. The process of claim 1 wherein the reaction step is carried out under a propylene pressure from approximately 1 to approximately 50 atmospheres.

10. The process of claim 9 wherein the propylene pressure is from approximately 1 to approximately 10 atmospheres.

* * * * *